(12) United States Patent
Andree et al.

(10) Patent No.: US 6,187,716 B1
(45) Date of Patent: Feb. 13, 2001

(54) HETEROCYCLYLURACIL

(75) Inventors: Roland Andree; Mark Wilhelm Drewes, both of Langenfeld; Wilhelm Haas, Pulheim, all of (DE); Markus Dollinger, Overland Park, KS (US)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/319,852

(22) PCT Filed: Dec. 5, 1997

(86) PCT No.: PCT/EP97/06819
§ 371 Date: Jun. 11, 1999
§ 102(e) Date: Jun. 11, 1999

(87) PCT Pub. No.: WO98/27082
PCT Pub. Date: Jun. 25, 1998

(30) Foreign Application Priority Data

Dec. 17, 1996 (DE) .............................. 196 52 429

(51) Int. Cl.$^7$ .......................... A01N 43/66; C07D 401/04
(52) U.S. Cl. .............................. 504/243; 544/310
(58) Field of Search .............................. 544/310; 504/243

(56) References Cited

U.S. PATENT DOCUMENTS

| | | | |
|---|---|---|---|
| 5,532,203 | 7/1996 | Fory et al. | 504/105 |
| 5,612,288 | 3/1997 | Fory et al. | 504/254 |
| 5,847,146 | 12/1998 | Schutz et al. | 546/309 |

FOREIGN PATENT DOCUMENTS

| | | |
|---|---|---|
| 3-287585 | 12/1991 | (JP) . |
| 5-202031 | 8/1993 | (JP) . |

OTHER PUBLICATIONS

Chem. Abstracts, vol. 120 No. 9, (1994) Abstract No. 107048v.
Chem. Abstracts, vol. 116, No. 28, (1992) Abstract No. 235650q.
Journal of Hetero. Chem. vol. 9, Jun. 1972, pp. 513–522.

*Primary Examiner*—John M. Ford
(74) *Attorney, Agent, or Firm*—Joseph C. Gil

(57) ABSTRACT

Novel heterocyclyluracils of the formula

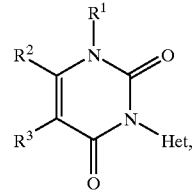

(I)

in which $R^1$, $R^2$, $R^3$ and Het are each as defined in the description, processes for preparing these substances and their use as herbicides.

7 Claims, No Drawings

HETEROCYCLYLURACIL

TECHNICAL FIELD OF THE INVENTION

The present invention relates to novel heterocyclyluracils, to a plurality of processes for their preparation and to their use as herbicides.

BACKGROUND OF THE INVENTION

Numerous heterocyclyluracils having herbicidal and/or insecticidal properties are already known (cf. JP-A 91-287 585, JP-A 93 202 031, Chem. Abstr. 116, 235 650 and Chem. Abstr. 120, 107 048). Thus, for example, 1-(3-chloro-5-trifluoromethyl-pyridin-2-yl)-3,6-dihydro-2,6-dioxo-4-trifluoromethyl-1(2H)-pyrimidine can be employed for controlling weeds. However, at low application rates, the activity of this substance is not always satisfactory.

DETAILED DESCRIPTION OF THE INVENTION

This invention, accordingly, provides novel heterocyclyluracils of the formula

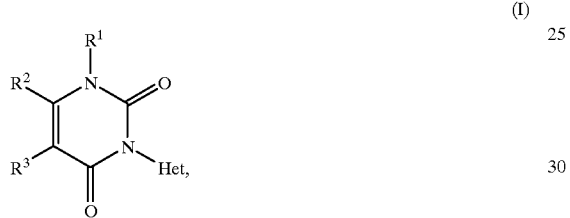

(I)

in which $R^1$ represents hydrogen or represents optionally cyano-, halogen- or $C_1$–$C_4$-alkoxy-substituted $C_1$–$C_4$-alkyl, $R^2$ represents formyl, hydroximinomethyl, cyano, carboxyl, alkoxycarbonyl, carbamoyl, thiocarbamoyl or represents optionally halogen-substituted $C_1$–$C_4$-alkyl, $R^3$ represents hydrogen, cyano, halogen or represents optionally halogen-substituted $C_1$–$C_4$-alkyl and Het represents the radical of the formula

in which $R^4$ represents hydroxyl, mercapto, amino, nitro, cyano, carbamoyl, thiocarbamoyl, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogeno-alkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety which is optionally mono- to trisubstituted by identical or different substituents from the group consisting of halogen, alkyl having 1 to 4 carbon atoms, dialkylamino having 1 to 4 carbon atoms in each alkyl group and alkoxy having 1 to 4 carbon atoms, $R^5$ represents hydroxyl, mercapto, amino, nitro, cyano, carboxyl, carbamoyl, halogen, alkyl having 1 to 6 carbon atoms, thiocarbamoyl, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety and being optionally mono- to trisubstituted by identical or different substituents from the group consisting of halogen, alkyl having 1 to 4 carbon atoms, dialkylamino having 1 to 4 carbon atoms in each alkyl group and alkoxy having 1 to 4 carbon atoms, and m represents integers from 0 to 3, or Het represents the radical of the formula

in which $R^6$ represents hydroxyl, mercapto, amino, carboxyl, carbamoyl, thiocarbamoyl, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety and being optionally mono- to trisubstituted by identical or different substituents from the group consisting of halogen, alkyl having 1 to 4 carbon atoms, dialkylamino having 1 to 4 carbon atoms in each alkyl group and alkoxy having 1 to 4 carbon atoms, $R^7$ represents hydroxyl, mercapto, amino, cyano, nitro, carboxyl, carbamoyl, thiocarbamoyl, halogen, alkyl having 1 to 6 carbon atoms, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety and being optionally mono- to trisubstituted by identical or different substituents from the group consisting of halogen, alkyl having 1 to 4 carbon atoms, dialkylamino having 1 to 4 carbon atoms in each alkyl group and alkoxy having 1 to 4 carbon atoms, and n represents integers from 0 to 3, or Het represents the radical of the formula

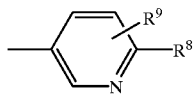

in which $R^8$ represents hydrogen, halogen, cyano, alkyl having 1 to 6 carbon atoms, halogenoalkyl having 1 to 4 carbon atoms and 1 to 5 halogen atoms or represents nitro and $R^9$ represents amino, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety and being optionally mono- to trisubstituted by identical or different substituents from the group consisting of halogen, alkyl having 1 to 4 carbon atoms, dialkylamino having 1 to 4 carbon atoms in each alkyl group and alkoxy having 1 to 4 carbon atoms.

Furthermore, it has been found that heterocyclyluracils of the formula (I) are obtained when a) aminoalkenoic esters of the formula

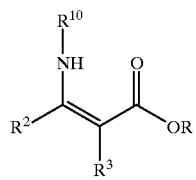

(II)

in which $R^2$ and $R^3$ are each as defined above, $R^{10}$ represents hydrogen or alkyl having 1 to 4 carbon atoms and R represents alkyl, aryl or arylalkyl are either α) reacted with heterocyclyl isocyanates of the formula

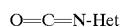

O=C=N-Het                (III), in which

Het is as defined above, or

β) reacted with heterocyclylcarbamates of the formula

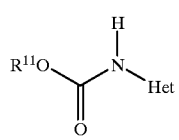

(IV)

in which

Het is as defined above and $R^{11}$ represents alkyl, aryl or arylalkyl, in each case if appropriate in the presence of an acid binder and if appropriate in the presence of a diluent, or b) heterocyclyluracils of the formula

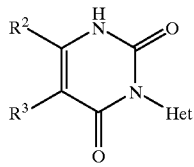

(Ia)

in which
R², R³ and Het are each as defined above
are either
    α) reacted with halogen compounds of the formula R¹²-Hal  (V)

in which
    $R_{12}$ represents alkyl having 1 to 4 carbon atoms which is optionally substituted by cyano, halogen or alkoxy having 1 to 4 carbon atoms and
    Hal represents chlorine, bromine or iodine,
or
    β) reacted with dialkyl sulphates of the formula

(VI)

in which
    $R^{13}$ represents alkyl having 1 to 4 carbon atoms,
in each case if appropriate in the presence of an acid binder and if appropriate in the presence of a diluent.

Finally, it has been found that the novel heterocyclyluracils of the formula (I) have very good herbicidal properties.

Surprisingly, the heterocyclyluracils of the formula (I) according to the invention have considerably better herbicidal activity than the constitutionally most similar active compounds of the prior art having the same direction of action.

In the present case, alkyl, alkoxy, alkylthio, alkylamino, dialkylamino, halogenoalkyl, halogenoalkoxy and halogenoalkylthio are in each case to be understood as straight-chain or branched radicals.

In the present case, halogen represents, unless stated otherwise, fluorine, chlorine, bromine or iodine. The formula (I) provides a general definition of the heterocyclyluracils according to the invention. Preference is given to compounds of the formula (I) in which
    $R^1$ represents hydrogen or represents optionally cyano-, fluorine-, chlorine-, methoxy- or ethoxy-substituted alkyl having 1 to 3 carbon atoms,
    $R^2$ represents formyl, hydroximinomethyl, cyano, carboxyl, alkoxycarbonyl having 1 to 4 carbon atoms in the alkoxy moiety, carbamoyl, thiocarbamoyl or represents alkyl having 1 to 3 carbon atoms which is optionally mono- to trisubstituted by identical or different substituents from the group consisting of fluorine and chlorine,
    $R^3$ represents hydrogen, cyano, fluorine, chlorine or represents alkyl having 1 to 3 carbon atoms which is optionally mono- to trisubstituted by identical or different substituents from the group consisting of fluorine and chlorine, and
Het represents the radical of the formula

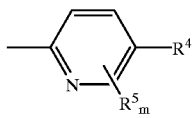

in which
    $R^4$ represents hydroxyl, mercapto, amino, cyano, nitro, carboxyl, carbamoyl, thiocarbamoyl, alkoxyalkyl having 1 to 4 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 to 4 carbon atoms, alkoxyalkoxy having 1 to 4 carbon atoms in each alkoxy moiety, alkylthio having 1 to 4 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 4 carbon atoms, dialkylamino having 1 to 4 carbon atoms in each alkyl moiety, halogenoalkylamino having 1 to 3 halogen atoms and 1 to 4 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoalkyl-carbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally 5 mono- to trisubstituted by identical or different substituents from the group consisting of fluorine, chlorine, bromine, methyl, ethyl, n-propyl, i-propyl, n-butyl, i-butyl, s-butyl, t-butyl, dimenthylamino, diethylamino, methoxy, ethoxy, n-propoxy and i-propoxy, $R^5$ represents hydroxyl, mercapto, amino, cyano, nitro, carboxyl, carbamoyl, thiocarbamoyl, fluorine, chlorine, bromine, iodine, alkyl having 1 to 4 carbon atoms, alkoxyalkyl having 1 to 4 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 to 4 carbon atoms, alkoxyalkoxy having 1 to 4 carbon atoms in each alkoxy moiety, alkylthio having 1 to 4 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 4 carbon atoms, dialkylamino having 1 to 4 carbon atoms in each alkyl moiety, halogenoalkylamino having 1 to 3 halogen atoms and 1 to 4 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonylamino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoalkylcarbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, n-propyl, i-propyl, n-butyl, i-butyl, s-butyl, t-butyl, dimenthylamino, diethylamino, methoxy, ethoxy, n-propoxy and i-propoxy, and m represents the numbers 0, 1 or 2, where $R^5$ represents identical or different radicals if m represents 2, or Het represents the radical of the formula

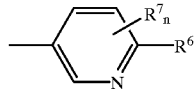

in which $R^6$ represents hydroxyl, mercapto, amino, carboxyl, carbamoyl, thiocarbamoyl, alkoxyalkyl having 1 to 4 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 to 4 carbon atoms, alkoxyalkoxy having 1 to 4 carbon atoms in each alkoxy moiety, alkylthio having 1 to 4 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 4 carbon atoms, dialkylamino having 1 to 4 carbon atoms in each alkyl moiety, halogenoalkylamino having 1 to 3 halogen atoms and 1 to 4 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkyl-sulphonyl-amino having 1 to 3 fluorine and/or chlorine atoms and 1 to 4 carbon atoms in the halogenoalkyl moiety of the halogenoalkylcarbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, n-propyl, i-propyl, n-butyl, i-butyl, s-butyl, t-butyl, dimenthylamino, diethylamino, methoxy, ethoxy, n-propoxy and i-propoxy, $R^7$ represents hydroxyl, mercapto, amino, cyano, nitro, carboxyl, carbamoyl, thiocarbamoyl, fluorine, chlorine, bromine, iodine, alkyl having 1 to 4 carbon atoms, alkoxyalkyl having 1 to 4 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 to 4 carbon atoms, alkoxyalkoxy having 1 to 4 carbon atoms in each alkoxy moiety, alkylthio having 1 to 4 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 4 carbon atoms, dialkylamino having 1 to 4 carbon atoms in each alkyl moiety, halogenoalkylamino having 1 to 3 halogen atoms and 1 to 4 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoalkylcarbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, n-propyl, i-propyl, n-butyl, i-butyl, s-butyl, t-butyl, dimenthylamino, diethylamino, methoxy, ethoxy, n-propoxy and i-propoxy, and n represents the numbers 0, 1 or 2, where $R^7$ represents identical or different radicals if n represents 2, or Het represents the radical of the formula

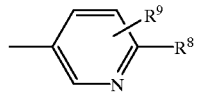

in which $R^8$ represents hydrogen, fluorine, chlorine, bromine, cyano, alkyl having 1 to 4 carbon atoms, halogenoalkyl having 1 or 2 carbon atoms and 1 to 5 fluorine and/or chlorine atoms or represents nitro, and $R^9$ represents amino, alkylamino having 1 to 4 carbon atoms, dialkylamino having 1 to 4 carbon atoms in each alkyl moiety, halogenoalkylamino having 1 to 3 halogen atoms and 1 to 4 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoalkyl-carbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, n-propyl, i-propyl, n-butyl, i-butyl, s-butyl, t-butyl, dimenthylamino, diethylamino, methoxy, ethoxy, n-propoxy and i-propoxy.

Particular preference is given to heterocyclyluracils of the formula (I), in which $R^1$ represents hydrogen, methyl, ethyl or difluoromethyl, $R^2$ represents carboxyl, methoxycarbonyl, cyano, carbamoyl, thiocarbonyl or represents methyl or ethyl, each of which is mono- to trisubstituted by identical or different substituents from the group consisting of fluorine and chlorine, $R^3$ represents hydrogen, fluorine, chlorine, bromine or methyl and Het represents the radical of the formula

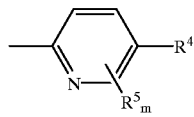

in which $R^4$ represents hydroxyl, mercapto, amino, cyano, nitro, carboxyl, carbamoyl, thiocarbamoyl, alkoxyalkyl having 1 or 2 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 or 2 carbon atoms, alkoxyalkoxy having 1 or 2 carbon atoms in each alkoxy moiety, alkylthio having 1 or 2 carbon atoms, halogenoalkylthio having 1 to 3 fluorine and/or chlorine atoms and 1 to 4 carbon atoms, alkylsulphinyl having 1 to 4 carbon atoms, halogenalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 3 carbon atoms, dialkylamino having 1 to 3 carbon atoms in each alkyl moiety, halogenoalkylamino having 1 to 3 fluorine and/or chlorine atoms and 1 to 3 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoalkylcarbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, dimethylamino, diethylamino, methoxy and ethoxy, $R^5$ represents hydroxyl, mercapto, amino, cyano, nitro, carboxyl, carbamoyl, thiocarbamoyl, fluorine, chlorine, bromine, iodine, alkyl having 1 to 4 carbon atoms, alkoxyalkyl having 1 or 2 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 or 2 carbon atoms, alkoxyalkoxy having 1 or 2 carbon atoms in each alkoxy moiety, alkylthio having 1 or 2 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 3 carbon atoms, dialkylamino having 1 to 3 carbon atoms in each alkyl moiety, halogenoalkylamino having 1 to 3 fluorine and/or chlorine atoms and 1 to 3 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogeno-alkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoaklyl carbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, dimethylamino, diethylamino, methoxy and ethoxy, and m represents the numbers 0, 1 or 2, where $R^5$ represents identical or different radicals if m represents 2, or Het represents the radical of the formula

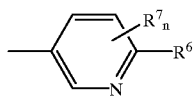

in which $R^6$ represents hydroxyl, mercapto, amino, carboxyl, carbamoyl, thiocarbamoyl, alkoxyalkyl having 1 or 2 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 or 2 carbon atoms, alkoxyalkoxy having 1 or 2 carbon atoms in each alkoxy moiety, alkylthio having 1 or 2 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 3 carbon atoms, dialkylamino having 1 to 3 carbon atoms in each alkyl moiety, halogenoalkylamino having 1 to 3 fluorine and/or chlorine atoms and 1 to 3 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoaklylcarbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, dimethylamino, diethylamino, methoxy and ethoxy, $R^7$ represents hydroxyl, mercapto, amino, cyano, nitro, carboxyl, carbamoyl, thiocarbamoyl, fluorine, chlorine, bromine, iodine, alkyl having 1 to 4 carbon atoms, alkoxyalkyl having 1 or 2 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 or 2 carbon atoms, alkoxyalkoxy having 1 or 2 carbon atoms in each alkoxy moiety, alkylthio having 1 or 2 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 3 carbon atoms, dialkylamino having 1 to 3 carbon atoms in each alkyl moiety, halogenoalkylamino having 1 to 3 fluorine and/or chlorine atoms and 1 to 3 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoalkylcarbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, dimethylamino, diethylamino, methoxy and ethoxy, and n represents the numbers 0, 1 or 2, where $R^7$ represents identical or different radicals if n represents 2, or Het represents the radical of the formula

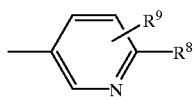

in which $R^8$ represents hydrogen, fluorine, chlorine, bromine, cyano, methyl, ethyl, n-propyl, isopropyl, n-butyl, sec-butyl, i-butyl, tert-butyl, trifluoro-methyl or nitro and $R^9$ represents amino, alkylamino having 1 to 3 carbon atoms, dialkylamino having 1 to 3 carbon atoms in each alkyl moiety, halogenoalkylamino having 1 to 3 fluorine and/or chlorine atoms and 1 to 3 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonyl-amino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkyl-carbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoaklyl-carbonyl group and having 1 to 3 fluorine and/or chlorine atoms and 1 to 4 carbon atoms in the halogenoalkylsulphonyl moiety or represents N-alkylsulphonyl-N-phenylcarbonyl-amino having 1 to 4 carbon atoms in the alkylsulphonyl moiety and being optionally mono- to trisubstituted by identical or different substituents from the group consisting of fluorine, chlorine, bromine, methyl, ethyl, dimethylamino, diethylamino, methoxy and ethoxy.

Very particular preference is given to heterocyclyluracils of the formula (I), in which $R^1$ represents hydrogen, methyl, ethyl or difluoromethyl, $R^2$ represents carboxyl, methoxycarbonyl, cyano, carbamoyl, thiocarbamoyl, methyl or trifluoromethyl, $R^3$ represents hydrogen and Het represents a heterocyclic radical of the formulae below:

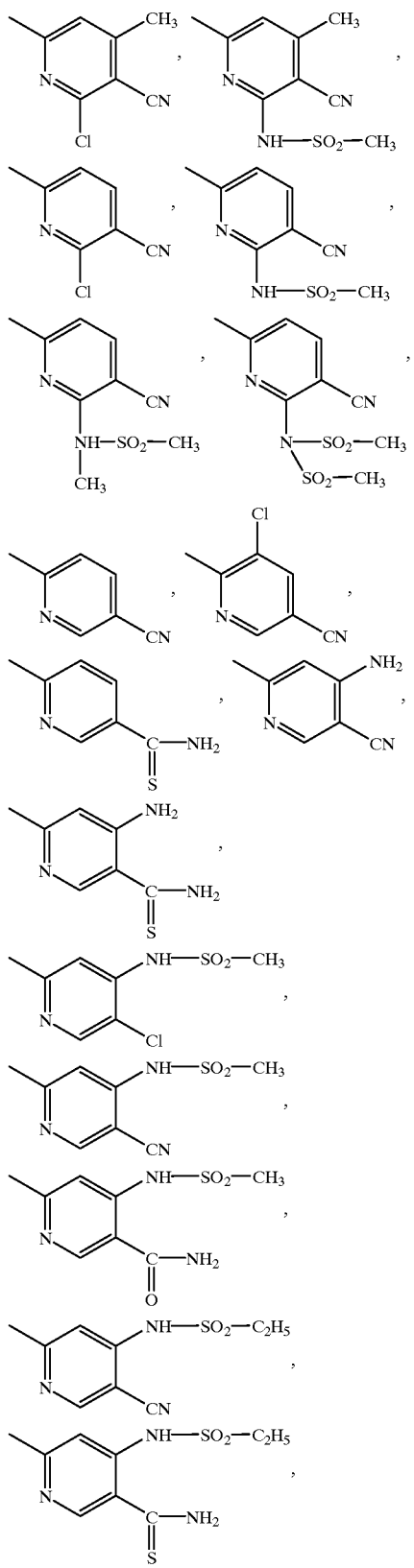

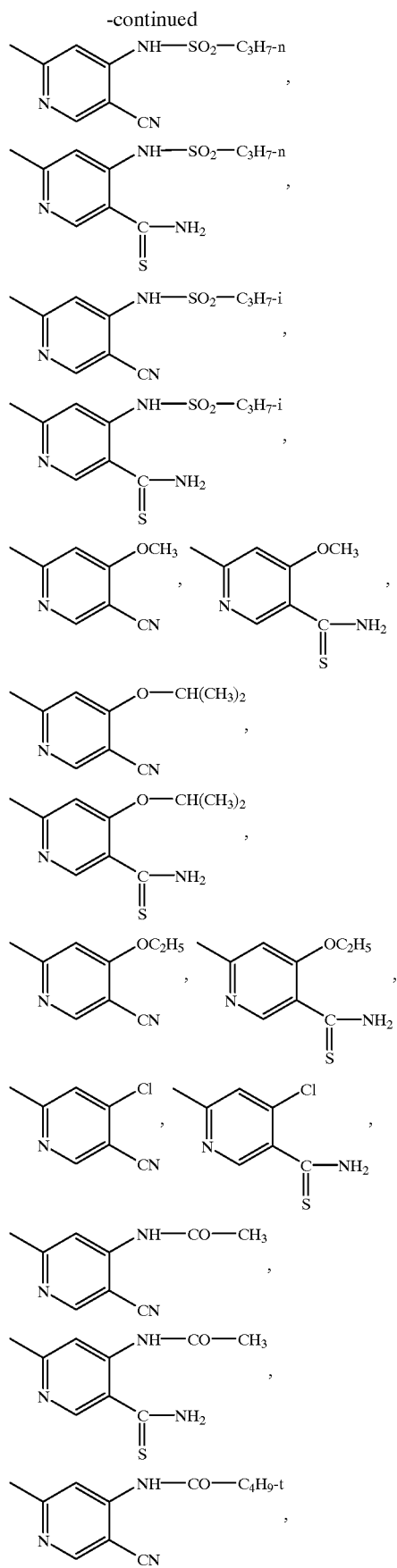
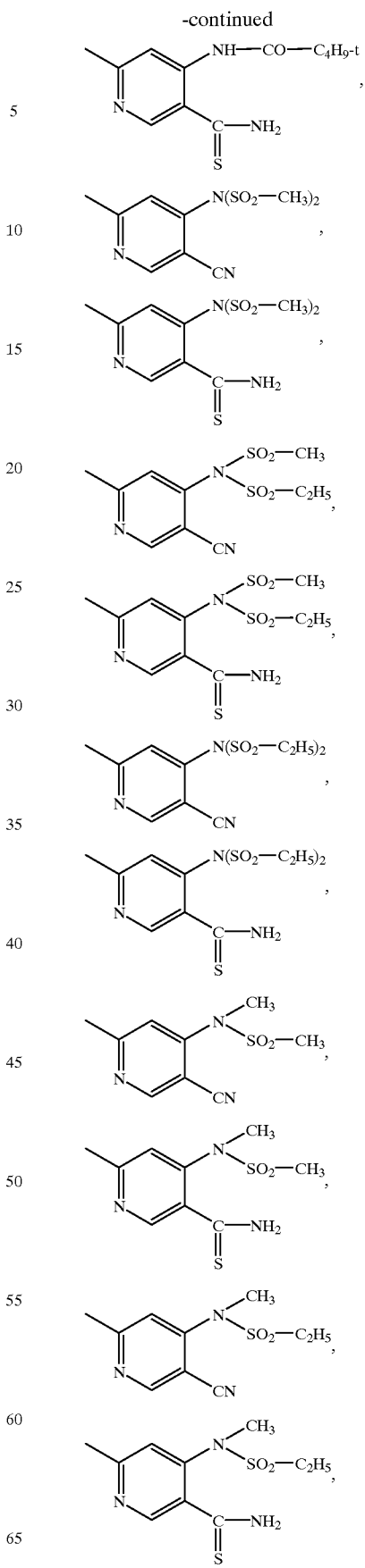

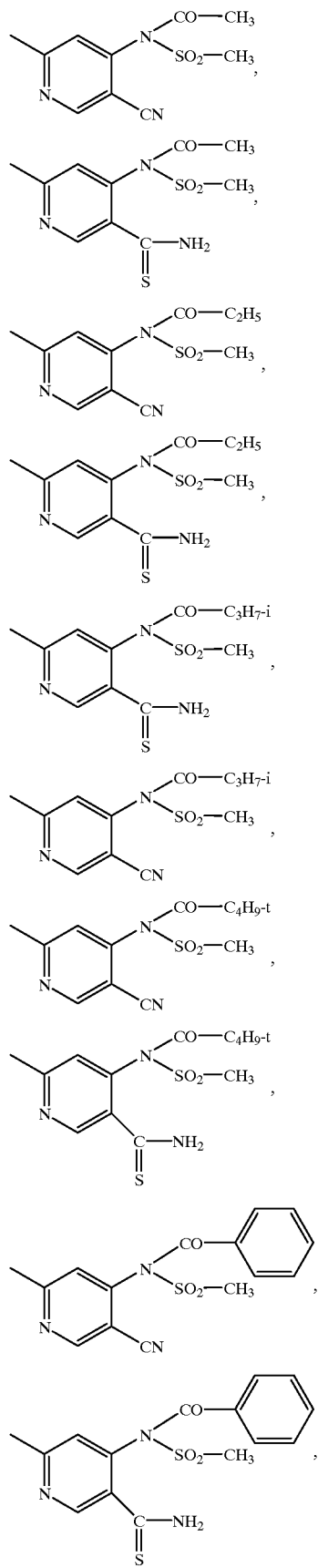
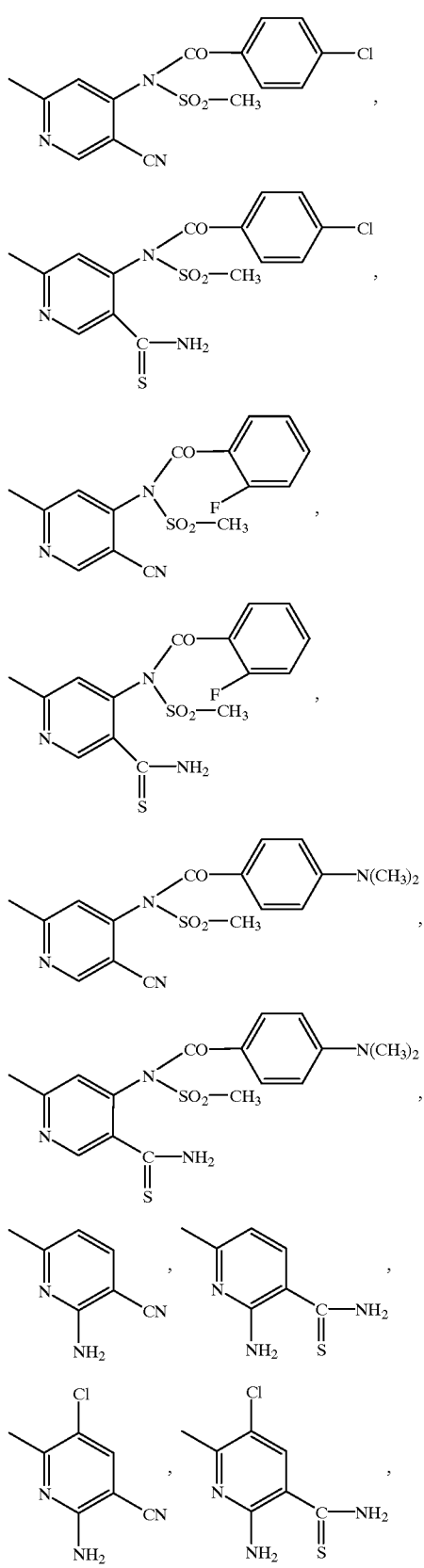

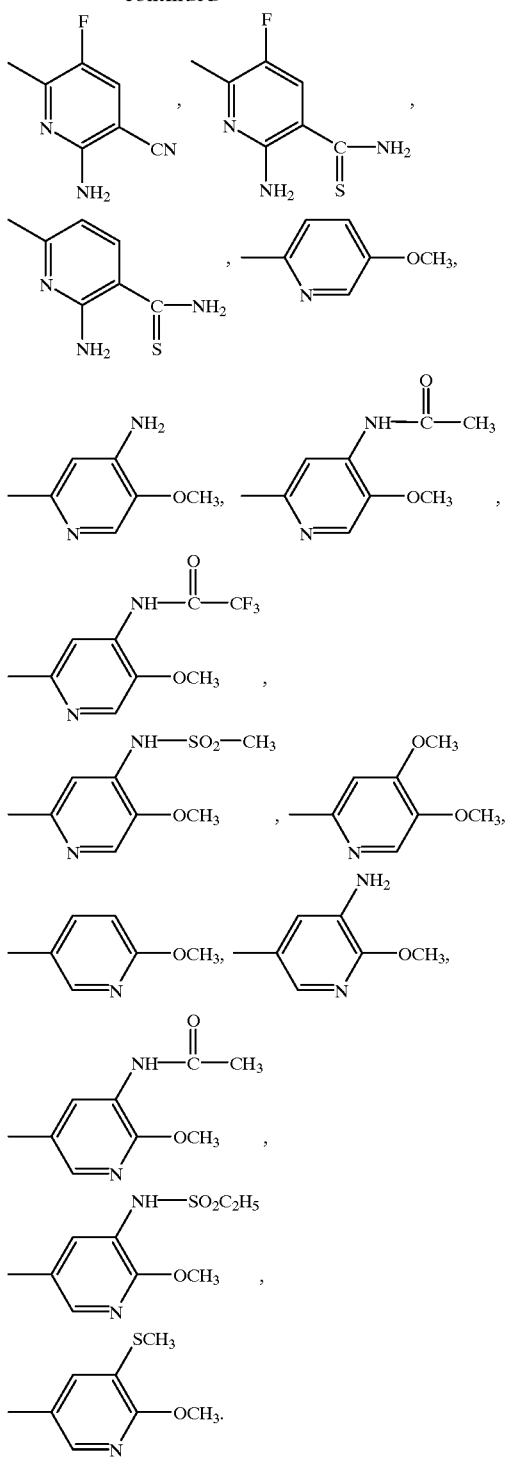

The abovementioned radical definitions apply both to the end products of the formula (I) and, correspondingly, to the starting materials or intermediates required in each case for the preparation. These radical definitions can be combined with each other at will, i.e. including combinations between the given ranges.

The heterocyclyluracils of the formula (I) according to the invention in which $R^1$ represents hydrogen can be present in the "keto" form of the formula

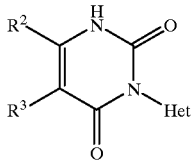

(Ia)

or in the tautomeric "enol" form of the formula

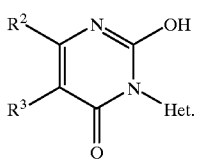

(Ib)

For the sake of simplicity, only the "keto" form is given in each case.

Using methyl 3-amino-crotonate and 3-chloro-2-thiocarbamoylpyridin-5-yl isocyanate as starting materials, the course of the process (a, variant α) according to the invention can be illustrated by the following equation:

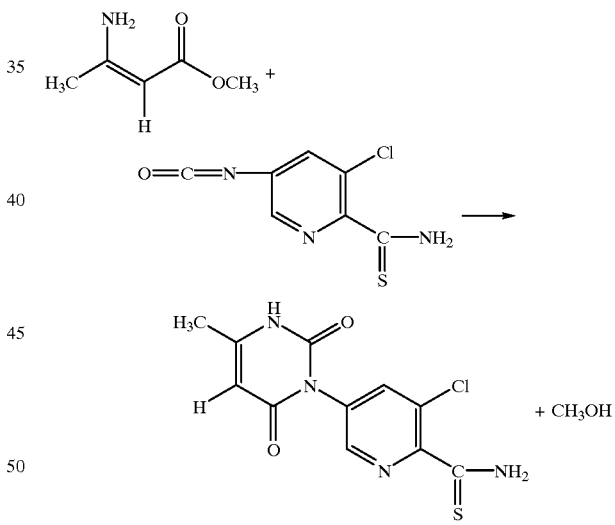

Using ethyl 3-amino-4,4,4-trifluorocrotonate and ethyl N-(2-chloro-3-cyano-4-methyl-pyridin-6-yl)-carbamate as starting materials, the course of the process (a, variant β) according to the invention can be illustrated by the following equation:

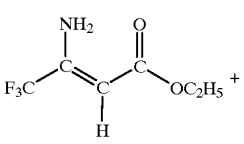

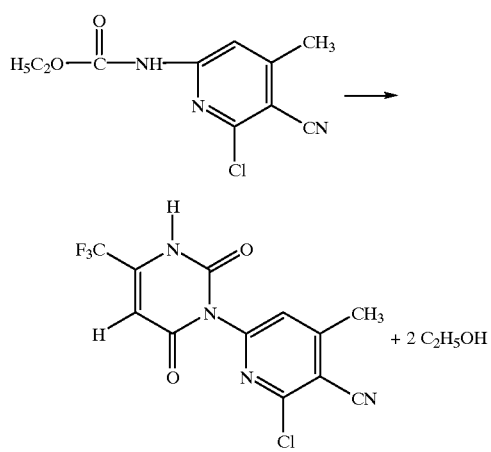

Using 1-(3-cyano-pyridin-6-yl)-3,6-dihydro-2,6-dioxo-4-tnfluoromethyl-1(2H)-py-rimidine as starting material and methyl iodide as reaction component, the course of the process (b, variant α) according to the invention can be illustrated by the following equation:

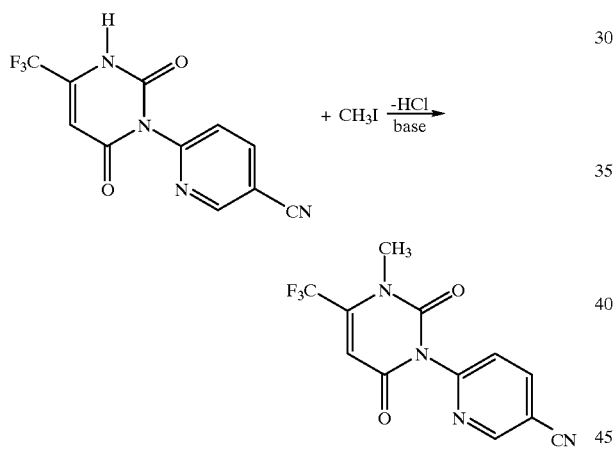

Using 1-(2-methoxy-pyridin-5-yl)-3,6-dihydro-2,6-dioxo-4-trifluoromethyl-1(2H)-pyrimidine as starting material and dimethyl sulphate as reaction component, the course of the process (b, variant β) according to the invention can be illustrated by the following equation:

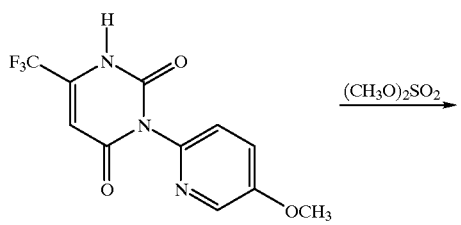

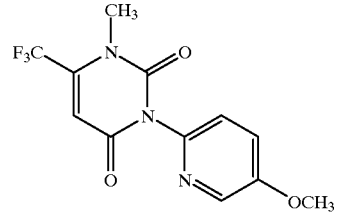

The formula (II) provides a general definition of the aminoalkenoic esters required as starting materials for carrying out the process (a) according to the invention. In the formula (II), $R^2$ and $R^3$ each preferably or in particular have those meanings which have already been indicated above, in connection with the description of the compounds of the formula (I) according to the invention, as being preferred or as being particularly preferred for $R^2$ and $R^3$. R preferably represents alkyl having 1 to 4 carbon atoms, phenyl or benzyl, particularly preferably represents methyl, ethyl, phenyl or benzyl. $R^{10}$ preferably represents alkyl having 1 to 3 carbon atoms, particularly preferably represents methyl or ethyl.

The aminoalkenoic esters of the formula (II) are known or can be prepared by processes known per se (cf. J. Heterocycl. Chem. 9 (1972), 513–522).

The formula (III) provides a general definition of the heterocyclyl isocyanates required as reaction components for carrying out the process (a, according to variant α) according to the invention. In the formula (III), Het preferably or in particular has those meanings which have already been mentioned above, in connection with the description of the compounds of the formula (I) according to the invention, as being preferred or as being particularly preferred for Het.

The heterocyclyl isocyanates of the formula (III) are known or can be prepared by processes known in principle (cf. EP-A 0 555 770 and EP-A 0 600 836). Thus, heterocyclyl isocyanates of the formula (III) can be prepared by reacting heterocyclylamines of the formula $$H_2N\text{-Het} \qquad (VII),$$

in which
Het is as defined above
with phosgene in the presence of a diluent, such as, for example, chlorobenzene, at temperatures between −20° C. and +150° C.

The heterocyclylamines of the formula (VII) are known or can be prepared by processes known in principle.

The formula (IV) provides a general definition of the heterocyclylcarbamates required as reaction components for carrying out the process (a, according to variant β) according to the invention. In the formula (IV), Het preferably or in particular has those meanings which have already been mentioned above, in connection with the description of the compounds of the formula (I) according to the invention, as being preferred or as being particularly preferred for Het. $R^{11}$ preferably represents $C_1$–$C_4$-alkyl, phenyl or benzyl, in particular represents methyl, ethyl or phenyl.

The heterocyclylcarbamates of the formula (IV) are known or can be prepared by processes known in principle (cf. EP-A 0 555 770 and EP-A 0 600 836). Thus, heterocyclylcarbamates of the formula (IV) are obtained when heterocyclylamines of the formula $$H_2N\text{-Het} \tag{VII}$$

in which

Het is as defined above are reacted with chlorocarbonyl compounds of the formula $$R^{11}O\text{—}CO\text{—}Cl \tag{VIII}$$

in which $R^{11}$ is as defined above, if appropriate in the presence of an acid acceptor, such as, for example, pyridine, and if appropriate in the presence of a diluent, such as, for example, methylene chloride, at temperatures between −20° C. and +100° C.

The formula (Ia) provides a general definition of the heterocyclyluracils required as starting materials for carrying out the process (b) according to the invention. These are substances that can be prepared by the process (a) according to the invention.

The formula (V) provides a general definition of the halogen compounds required as reaction components for carrying out the process (b, variant α) according to the invention. In this formula, $R^{12}$ preferably represents optionally cyano-, fluorine-, chlorine-, methoxy- or ethoxy-substituted alkyl having 1 to 3 carbon atoms. Hal preferably represents bromine or iodine.

Particularly preferably utilizable are halogen compounds of the formula (V) in which $R^{12}$ represents methyl, ethyl or difluoromethyl and Hal represents bromine or iodine.

The halogen compounds of the formula (V) are known or can be prepared by processes known in principle.

The formula (VI) provides a general definition of the dialkyl sulphates required as reaction components for carrying out the process (b, variant β) according to the invention. In this formula, $R^{13}$ preferably represents alkyl having 1 to 3 carbon atoms, particularly preferably represents methyl or ethyl.

The dialkyl sulphates of the formula (VI) are known.

Suitable acid acceptors for carrying out the process (a) according to the invention, both by variant (α) and by variant (β), are all customary inorganic and organic bases. Preference is given to using alkali metal or alkaline earth metal acetates, amides, carbonates, bicarbonates, hydrides, hydroxides or alkoxides, such as sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as trimethylamine, triethylamine, tripropylamine, tributylamine, ethyl-diisopropylamine, N,N-dimethyl-cyclohexylamine, dicyclohexylamine, ethyldicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylaminopyridine, N-methyl-piperidine, 1,4-diazabicyclo[2,2,2]-octane (DABCO), 1,5-diazabicyclo[4,3,0]-non-5-ene (DBN) or 1,8 diazabicyclo[5,4,0]-undec-7-ene (DBU).

Suitable diluents for carrying out the process (a) according to the invention by variants (α) or (β) are all customary inert, organic solvents, and also water. Preference is given to using aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methyl-pyrrolidone or hexamethylphosphoric triamide; esters such as methyl acetate or ethyl acetate, or sulphoxides, such as dimethyl sulphoxide.

When carrying out the process (a) according to the invention, the reaction temperatures can be varied within a relatively wide range. Both variant (α) and variant (β) are generally carried out between 0° C. and 200° C., preferably between 10° C. and 150° C.

The process (a) according to the invention, by variant (α) and (β), is generally carried out under atmospheric pressure. However, in each case it is also possible to operate under elevated or reduced pressure, for example between 0.1 and 10 bar.

When carrying out the process (a) according to the invention, in the case of variant (α), an approximately equimolar amount of heterocyclyl isocyanate of the formula (III) and, in the case of variant (β), an approximately equimolar amount of heterocyclylcarbamate of the formula (IV) is employed per mole of aminoalkenoic ester of the formula (II). However, it is also possible to employ a relatively large excess of in each case one of the components. The reactions are generally carried out in a suitable diluent in the presence of an acid binder. The reaction mixture is stirred at the required temperature as long as required and is then worked up by customary methods.

Suitable acid binders for carrying out the process (b) according to the invention, by variant (α) or (β), are all customary inorganic and organic bases. Preference is given to using those acid acceptors which have already been mentioned, in connection with the description of the process (a) according to the invention, as being preferred.

Suitable diluents for carrying out the process (b) according to the invention, by variant (α) or (β), are all inert organic solvents which are customary for such reactions. Preference is given to using nitriles, such as acetonitrile and butyronitrile, furthermore ketones, such as acetone, and also amides, such as dimethylformamide and N-methylpyrrolidone.

When carrying out the process (b) according to the invention, the reaction temperatures can likewise be varied within a relatively wide range.

The variant (α) is generally carried out at temperatures between 0° C. and 150° C., preferably between 10° C. and 120° C., the variant (β) is generally carried out at temperatures between 10° C. and 100° C., preferably between 15° C. and 80° C.

The process (b) according to the invention, by variant (α) and (β), is likewise generally carried out under atmospheric pressure. However, it is also possible to operate in each case under elevated or, if there are no volatile components participating in the reaction, under reduced pressure.

When carrying out the process (b) according to the invention by variant (α) or (β), in general an approximately equimolar amount of halogen compound of the formula (V) or of dialkyl sulphate of the formula (VI) is employed per mole of heterocyclyluracil of the formula (Ia). However, it is also possible to employ a relatively large excess of in each case one of the components. Work-up is in each case carried out by customary methods.

The active compounds according to the invention exhibit very good herbicidal activity and can be used as defoliants, desiccants, haulm killers and, especially, as weed-killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:
Dicotyledonous Weeds of the Genera: Sinapis, Lepidium, Galium, Stellaria, Matricaria, Anthemis, Galinsoga, Chenopodium, Urtica, Senecio, Amaranthus, Portulaca, Xanthium, Convolvulus, lpomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.
Dicotyledonous Crops of the Genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.
Monocotyledonous Weeds of the Genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.
Monocotyledonous Crops of the Genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual cultures.

The compounds of the formula (I) according to the invention are suitable in particular for selectively controlling monocotyledonous and dicotyledonous weeds in monocotyledonous crops, both pre-emergence and post-emergence. Additionally, they are tolerated well by important crop plants, such as maize and wheat.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to use, for example, organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or di-atomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and also granules of organic material such as sawdust, coconut shells, maize cobs and tobacco stalks; suitable emulsifiers and/or foam-forrning agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible. In some cases, synergism may also occur.

Possible components for the mixtures are, for example, the following herbicides: acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulftiron(-methyl), ethofumesate, ethoxyfen, etobenzanid, fenoxaprop(-ethyl), flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium), quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

Example 1

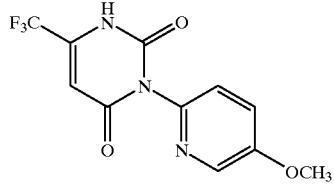

At 100° C., a mixture of 26.6 g (135 mmol) of ethyl 3-amino-4,4,4-trifluorocrotonate, 24.6 g of potassium carbonate and 200 ml of N-methyl-pyrrolidone is stirred under nitrogen for one hour. 17.5 g (90 mmol) of O-ethyl N-(2-methoxy-pyridin-5-yl)-carbamate are then added, and the reaction mixture is heated at approximately 130° C. on a water separator for four hours. Under nitrogen, the mixture is allowed to cool to room temperature and then poured into 1 l of water and extracted three times with 100 ml of methylene chloride each time. After acidification with concentrated hydrochloric acid (to a pH of 3), the mixture is allowed to stand for one hour and the crystalline product is isolated by filtration with suction.

This gives 18.2 g (71% of theory of 1-(2-methoxy-pyridin-5-yl)-3,6-dihydro-2,6-dioxo-4-trifluoromethyl-1 (2H)-pyrimidine of melting point 152° C.

Preparation of the Starting Material of the Formula (IV-I)

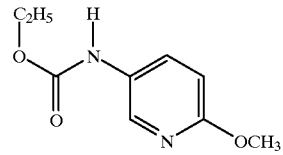

At room temperature, 11 g (0.1 mol) of ethyl chloroformate are added dropwise with stirring to a mixture of 12.4 g (0.1 mol) of 2-methoxy-5-amino-pyridine, 15,8 g of pyridine and 100 ml of methylene chloride. The reaction mixture is stirred at room temperature for three hours and then washed with IN hydrochloric acid, dried with sodium sulphate and filtered through silica gel. From the filtrate, the solvent is carefully distilled off under reduced pressure. This gives 17.9 g of O-ethyl N-(2-methoxy-pyridin-5-yl)-carbamate as a crystalline product of melting point 76° C.

Example 2

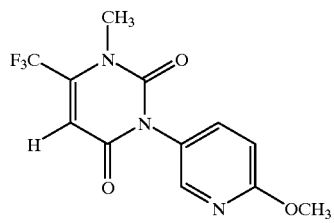

A mixture of 4.0 g (14 mmol) of 1-(2-methoxy-pyridin-5-yl)-3,6-dihydro-2,6-dioxo-4-trifluoromethyl-1(2H)-pyrimidine, 1.9 g (15 mmol) of dimethyl sulphate, 1.3 g of sodium bicarbonate and 100 ml of acetone is heated under reflux for 18 hours. The mixture is concentrated under water pump vacuum and the residue is then shaken with water/methylene chloride. The organic phase is separated off, dried with sodium sulphate and filtered through silica gel. The filtrate is concentrated under water pump vacuum, the residue is digested with diethyl ether and the resulting crystalline product is isolated by filtration with suction.

This gives 3.0 g (54% of theory) of 1-(2-methoxy-pyridin-5-yl)-3,6-dihydro-2,6-dioxo-3-methyl-4-trifluoromethyl-1(2H)-pyrimidine of melting point 130° C.

The compounds of the formula (I) listed in Table 1 below are prepared by the methods given above.

TABLE 1

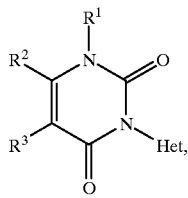
(I)

| Ex. No. | R¹ | R² | R³ | Het | Melting point (° C.) |
|---|---|---|---|---|---|
| 3 | H | CF₃ | H | 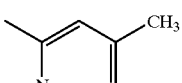 | 190 |
| 4 | CH₃ | CF₃ | H |  | 144 |
| 5 | H | CF₃ | H | 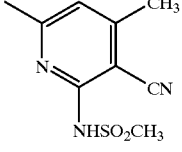 | (amorphous) |
| 6 | H | CF₃ | H | 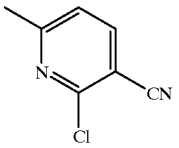 | 150 |
| 7 | CH₃ | CF₃ | H | 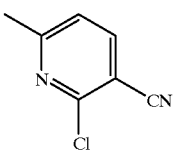 | 150 |
| 8 | H | CF₃ | H | 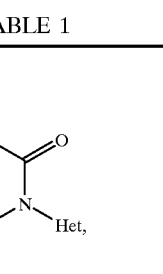 | 275 |
| 9 | CH₃ | CF₃ | H | 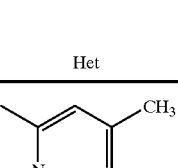 | 221 |
| 10 | H | CF₃ | H | 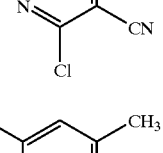 | 267 |
| 11 | H | CF₃ | H | 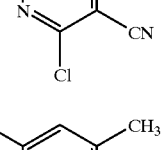 | 255 |
| 12 | CH₃ | CF₃ | H | 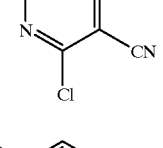 | 180 |
| 13 | H | CF₃ | H | 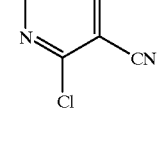 | 235 |

TABLE 1-continued (I)

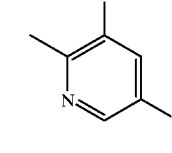

| Ex. No. | R¹ | R² | R³ | Het | Melting point (° C.) |
|---|---|---|---|---|---|
| 14 | CH₃ | CF₃ | H | 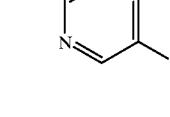 | 225 |
| 15 | H | CF₃ | H | 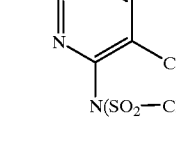 | 160 |
| 16 | H | CF₃ | H | 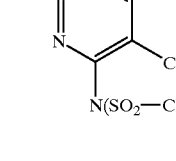 | 250 |
| 17 | CH₃ | CF₃ | H | 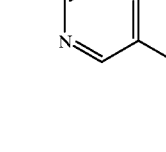 | 275 |
| 18 | CH₃ | CF₃ | H |  | 158 |
| 19 | CH₃ | CF₃ | H | (image: pyridine with N(SO₂C₂H₅)₂ and Cl) | |

TABLE 1-continued (I)

| Ex. No. | R¹ | R² | R³ | Het | Melting point (° C.) |
|---|---|---|---|---|---|
| 20 | CH₃ | CF₃ | H | (pyridine with NHSO₂C₂H₅, Cl) | |
| 21 | CH₃ | CF₃ | H | (pyridine with CN, N(SO₂CH₃)₂) | 259 |
| 22 | CH₃ | CF₃ | H | (pyridine with CN, NHSO₂CH₃) | 238 |
| 23 | CH₃ | CF₃ | H | (pyridine with C(S)NH₂, NHSO₂CH₃) | 250 |
| 24 | CH₃ | CF₃ | H | (pyridine with C(S)NH₂, N(SO₂CH₃)₂) | 265 |

USE EXAMPLES

Example A

Pre-emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered with the preparation of the active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

| |
|---|
| 0% = no effect (like untreated control) |
| 100% = total destruction |

In this test, the compounds of Preparation Examples 7 and 9 exhibit, at application rates of 125 to 250 g/ha, strong activity against weeds, and they are in some instances well tolerated by crop plants, such as maize and soybean.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison to the development of the untreated control.

TABLE A

| Pre-emergence test/greenhouse | | | | | | |
|---|---|---|---|---|---|---|
| Active compound of Ex. No. | Application rate (g of ai.h) | Maize | Soy-bean | Cheno-podium | Materi-caria | Solanum |
| 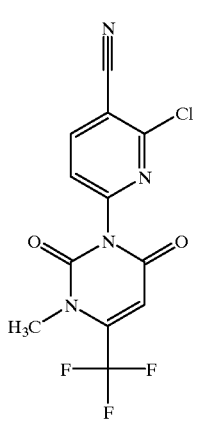 | 125 | 0 | 10 | 95 | 95 | 100 |

| Active compound of Ex. No. | Application rate (g of ai.h) | Setaria | Abutilon | Amaranthus | Sinapis |
|---|---|---|---|---|---|
| 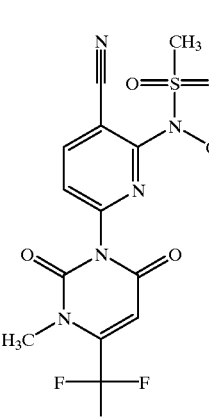 | 250 | 100 | 100 | 100 | 100 |

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The figures denote:

| |
|---|
| 0% = no effect (like untreated control) |
| 100% = total destruction |

In this test, the compounds of Preparation Examples 7 and 9 exhibit, at application rates of 60 to 250 g/ha, strong activity against weeds, and they are in some instances tolerated well by crop plants, such as wheat.

TABLE B

| Post-emergence test/greenhouse | | | | | | |
|---|---|---|---|---|---|---|
| Active compound of Ex. No. | Application rate (g of ai.h) | Wheat | Amaranthus | Datura | Polygonum | Solanum |
| 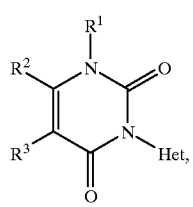 | 60 | 10 | 100 | 100 | 100 | 100 |

| Active compound of Ex. No. | Application rate (g of ai.h) | Setaria | Abutilon | Amaranthus | Sinapis |
|---|---|---|---|---|---|
| 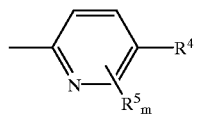 | 250 | 90 | 100 | 100 | 100 |

What is claimed is:

1. A heterocyclyluracil of the formula (I)

wherein $R^1$ represents hydrogen or represents unsubstituted or cyano-, halogen- or $C_1$–$C_4$-alkoxy-substituted $C_1$–$C_4$-alkyl, $R^2$ represents formyl, hydroximinomethyl, cyano, carboxyl, alkoxycarbonyl, carbamoyl, thiocarbamoyl or represents unsubstituted or halogen-substituted $C_1$–$C_4$-alkyl, $R^3$ represents hydrogen, cyano, halogen or represents unsubstituted or halogen-substituted $C_1$–$C_4$-alkyl and Het represents the radical of the formula wherein $R^4$ represents hydroxyl, mercapto, amino, nitro, cyano, carbamoyl, thiocarbamoyl, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety which is unsubstituted or mono- to trisubstituted by identical or different substituents selected from the group consisting of halogen, alkyl having 1 to 4 carbon atoms, dialkylamino having 1 to 4 carbon atoms in each alkyl group and alkoxy having 1 to 4 carbon atoms, $R^5$ represents hydroxyl, mercapto, amino, nitro, cyano, carboxyl, carbamoyl, thiocarbamoyl, halogen, alkyl having 1 to 6 carbon atoms, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety and being unsubstituted or mono- to trisubstituted by identical or different substituents selected from the group consisting of halogen, alkyl having 1 to 4 carbon atoms, dialkylamino having 1 to 4 carbon atoms in each alkyl group and alkoxy having 1 to 4 carbon atoms, and m represents integers from 0 to 3, or Het represents the radical of the formula wherein $R^6$ represents hydroxyl, mercapto, amino, carboxyl, carbamoyl, thiocarbamoyl, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety and being unsubstituted or mono- to trisubstituted by identical or different substituents selected from the group consisting of halogen, alkyl having 1 to 4 carbon atoms, dialkylamino having 1 to 4 carbon atoms in each alkyl group and alkoxy having 1 to 4 carbon atoms, $R^7$ represents hydroxyl, mercapto, amino, cyano, nitro, carboxyl, carbamoyl, halogen, alkyl having 1 to 6 carbon atoms, thiocarbamoyl, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety and being unsubstituted or mono- to trisubstituted by identical or different substituents selected from the group consisting of halogen, alkyl having 1 to 4 carbon atoms, dialkylamino having 1 to 4 carbon atoms in each alkyl group and alkoxy having 1 to 4 carbon atoms, and n represents integers from 0 to 3, or Het represents the radical of the formula

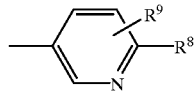

wherein $R^8$ represents hydrogen, halogen, cyano, alkyl having 1 to 6 carbon atoms, halogenoalkyl having 1 to 4 carbon atoms and 1 to 5 halogen atoms or represents nitro and $R^9$ represents amino, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkyl-sulphonyl-amino having 1 to 5 halogen atoms and 1 to 6 carbon atoms in each halogenoalkyl moiety, N-alkyl-N-alkylsulphonylamino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety or represents N-alkylsulphonyl-N-phenylcarbonyl-amino having 1 to 6 carbon atoms in the alkylsulphonyl moiety and being unsubstituted or mono- to trisubstituted by identical or different substituents selected from the group consisting of halogen, alkyl having 1 to 4 carbon atoms, dialkylamino having 1 to 4 carbon atoms in each alkyl group and alkoxy having 1 to 4 carbon atoms.

2. A herbicidal composition comprising at least one heterocyclyluracil of the formula (I) according to claim 1 and one or more extenders and/or surfactants.

3. A method for controlling weed, comprising the step of applying an effective amount of a heterocyclyluracil of the formula (I) according to claim 1 to the weeds and/or their habitat.

4. A process for preparing a heterocyclyluracil of the formula (I) according to claim 1, comprising the steps of:

a) reacting an aminoalkenoic ester of the formula (II)

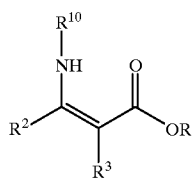

(II)

wherein
$R^2$ and $R^3$ are each as defined in claim 1,
$R^{10}$ represents hydrogen or alkyl having 1 to 4 carbon atoms, and R represents alkyl, aryl or arylalkyl, with a heterocyclylcarbamate of the formula (IV)

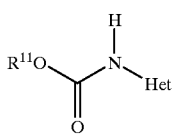

(IV)

wherein
Het is as defined in claim 1, and
$R^{11}$ represents alkyl, aryl or arylalkyl; and b) reacting the resultant compound from step a) of the formula (Ia)

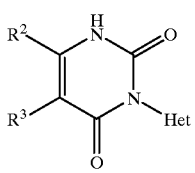

(Ia)

wherein
$R^2$, $R^3$ and Het are each as defined in claim 1, with a halogen compound of the formula (V)

$$R^{12}\text{-Hal} \qquad (V)$$

wherein
$R^{12}$ represents alkyl having 1 to 4 carbon atoms which is unsubstituted or substituted by cyano, halogen or alkoxy having 1 to 4 carbon atoms and
Hal represents chlorine, bromine or iodine.

5. The process of claim 4 wherein the reaction is carried out in the presence of an acid binder.

6. The process of claim 4 wherein the reaction is carried out in the presence of a diluent.

7. The process of claim 4 wherein the reaction is carried out in the presence of a diluent and an acid binder.

* * * * *